United States Patent [19]
Matsuo

[11] 4,182,558
[45] Jan. 8, 1980

[54] CAMERA MOUNTING DEVICE FOR AN ENDOSCOPE

[75] Inventor: Kazumasa Matsuo, Hachioji, Japan

[73] Assignee: Olympus Optical Co., Ltd., Tokyo, Japan

[21] Appl. No.: 861,408

[22] Filed: Dec. 16, 1977

[30] Foreign Application Priority Data

Dec. 25, 1976 [JP] Japan ............................ 51-174314[U]

[51] Int. Cl.$^2$ ...................... G03B 17/00; G03B 29/00; E16D 1/10
[52] U.S. Cl. ....................................... 354/62; 354/293; 403/316; 403/DIG. 4
[58] Field of Search ...................... 354/293, 62, 63, 79, 354/81, 82; 285/5, 7; 403/316, 318, DIG. 4, 322; 128/4

[56] References Cited

U.S. PATENT DOCUMENTS

| | | | |
|---|---|---|---|
| 2,245,151 | 6/1941 | Martinet | 285/7 |
| 2,267,802 | 12/1941 | Purdy | 403/316 |
| 3,569,903 | 3/1971 | Brishka | 403/322 X |
| 3,900,021 | 8/1975 | Makepeace et al. | 128/4 |
| 3,922,011 | 11/1975 | Walters | 403/322 X |
| 4,067,025 | 1/1978 | Nebel et al. | 354/62 |

FOREIGN PATENT DOCUMENTS

| | | | |
|---|---|---|---|
| 2417814 | 10/1975 | Fed. Rep. of Germany | 354/62 |
| 1210943 | 3/1960 | France | 403/DIG. 4 |
| 143572 | 4/1961 | U.S.S.R. | 354/63 |

Primary Examiner—L. T. Hix
Assistant Examiner—Thomas H. Tarcza

[57] ABSTRACT

A camera mounting device for an endoscope consists of a hollow connecting tube provided at one end with a camera mount and at the other end with a cavity for receiving an ocular portion of the endoscope having a conical rear surface, engaging elements pivoted to the other end of the connecting tube and circumferentially spaced from each other in the cavity so as to normally press the conical rear surface of the ocular portion thereby to hold the ocular portion in the cavity, and a releasing mechanism for rotating the engaging elements out of the cavity, whereby connection and disconnection of the camera mounting device to and from the ocular portion of the endoscope can be made by a single-handed operation of an operator.

4 Claims, 2 Drawing Figures

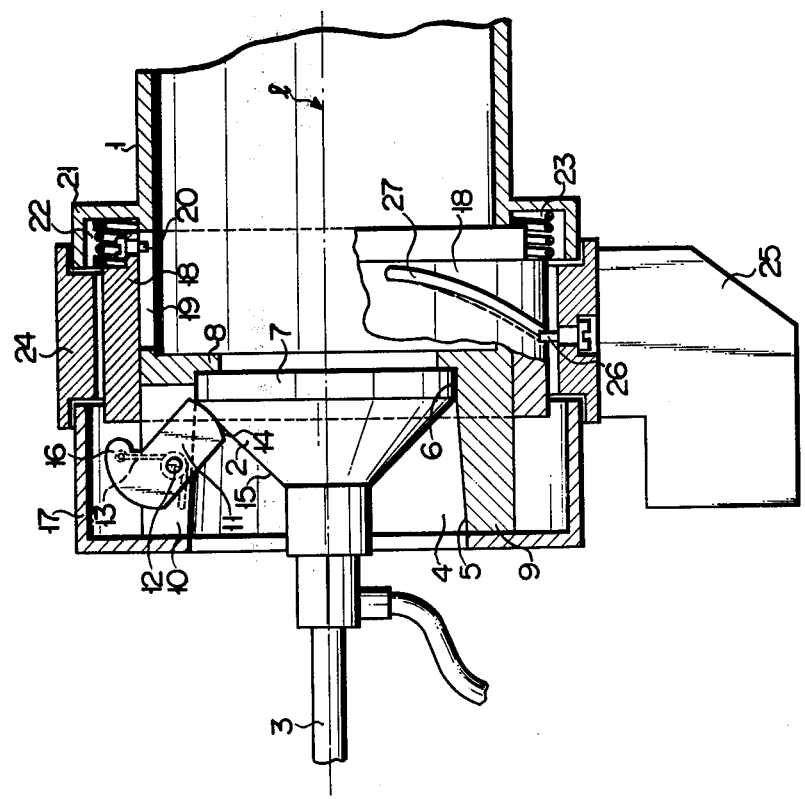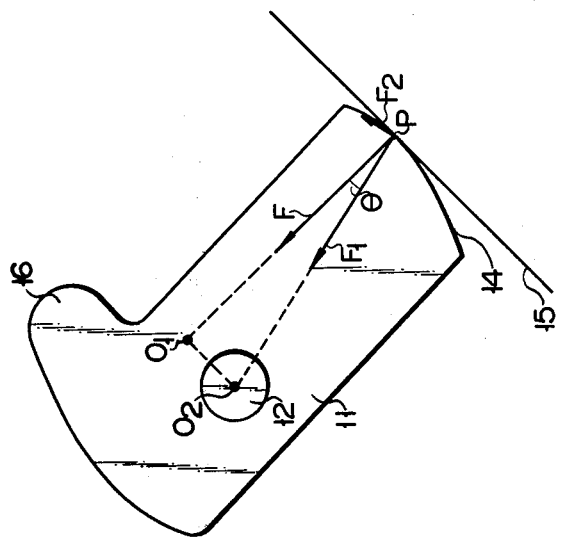

CAMERA MOUNTING DEVICE FOR AN ENDOSCOPE

BACKGROUND OF THE INVENTION

1. Field of the Invention

This invention relates to a camera mounting device for an endoscope which enables an operator to easily attach and detatch a camera to and from an ocular portion of an endoscope.

2. Description of the Prior Art

When a coelom is examined by means of an endoscope, it is very important to take at any required time photographs of the affected parts of the coelom for the diagnosis and treatment of intra-coeliac deseases.

Conventional camera mounting devices for an endoscope are also detatchably connected to the ocular portion of the endoscope. However, attaching and detatching of the prior art devices are achieved in a relatively complicated manner such as screw engagement, and thus cannot be undertaken by an operator alone. The operator, therefore, needs an assistant.

Since the intra-coeliac photographing must be conducted in any positions and at any time, it is strongly desired that a camera be attached to the ocular portion of an endoscope speedily and easily as well as by a single-handed operation of an operator without any assistant's help.

SUMMARY OF THE INVENTION

An object of this invention is to provide a camera mounting device for an endoscope enabling an operator to accomplish speedy and easy single-handed attaching and detaching of a camera to and from the ocular portion of an endoscope.

Another object of the invention is to provide a camera mounting device for an endoscope which would not easily come off the ocular portion even if it is exerted by any force to separate it from the ocular portion coupled therewith.

A camera mounting device for an endoscope according to this invention comprises a hollow connecting tube having one end fitted with a camera mount, a cavity defined in the other end portion of the tube for locating an ocular portion of the endoscope, engaging elements pivoted to said other end portion of the tube, each normally engaged at an engaging surface thereof with a conical rear surface of the ocular portion by an urging means so as to hold the ocular portion in the cavity, and a releasing means disposed at said other end portion of the tube to rock the engaging elements to the outside of the cavity against the urging means. In this construction, the device can be attached to the endoscope only by pressing the ocular portion against a wall of the cavity, and can be easily removed from the endoscope by actuating the releasing means, so that an operator can unfailingly handle the device by a single hand.

BRIEF DESCRIPTION OF THE DRAWINGS

This invention may be fully understood from the following detailed description with reference to the accompanying drawings, in which:

FIG. 1 is a sectional view of the principal portion of an embodiment of a camera mounting device for an endoscope according to this invention, and FIG. 2 is an explanatory sketch illustrating the operation of an engaging element of the camera mounting device of FIG. 1.

DETAILED DESCRIPTION OF THE PREFERRED EMBODIMENT

Referring now to FIG. 1, a camera mounting device for an endoscope is provided with a hollow cylindrical connecting tube 1 fitted at one end thereof with a camera mount (not shown). An ocular portion or an eyepiece 2 provided on the proximal end portion 3 of an endoscope is inserted in a cavity 4 formed in the other end portion of the tube 1. The cavity 4 is defined by a truncated-cone-shaped wall surface 5 diverging outward and a cylindrical inner wall surface 6 with its innermost portion complementary to an outer peripheral edge portion 7 of the ocular portion 2. The cylindrical inner wall surface 6 is continuous to a flange 8 extending inward from the inner wall surface of the tube 1. The front of the outer peripheral edge portion 7 of the ocular portion 2 is brought in contact with the opposite surface of the flange 8. In a cylindrical adapting portion 9 whose inner surface defines the wall surfaces 5 and 6 of the cavity 4, there are formed a plurality of (e.g., three) slits 10 (only one shown in FIG. 1) extending along the central axis l of the tube 1 (which is also an optical axis thereof) and arranged in circumferential spaced relation with each other. In each of the slits 10 is disposed an engaging element 11 rockable about a pivot 12 fixed to the adapting portion 9. Each of the elements 11 is urged clockwise in FIG. 1 by an urging means such as a tension spring 13. A convex cam surace or engaging surface 14 formed at that end of the element 11 which faces the central axis l is pressed against a conical rear surface 15 of the ocular portion 12, thereby bringing the front end surface of the edge portion 7 of the ocular portion 2 into close contact with the end surface of the flange 8 opposed thereto and holding the ocular portion 2 in a prescribed position in the cavity 4. Formed at the other end or outer end of the engaging element 11 is a projecting portion 16 extending toward the camera mount. A ring-shaped end member 17 is fixed at its end wall to the end of the adapting portion 9 of the tube 1 so as to surround and protect the portion 9 and the engaging elements.

A cylindrical cam or cylindrical member 18 surrounds said other end of the tube 1. A slot 19 extending along the central axis l of the tube 1 is formed in the wall of the tube 1 within the range covered by the cam 18, and a pin 20 protruding inward from the cam 18 is inserted in the slot 19 so that the cam 18 can reciprocate axially of the tube 1. A rim 21 is formed on the outer periphery of the tube 1, and a tension spring 23 is disposed in a chamber 22 defined by the rim 21 so as to normally urge the cam 18 toward the camera mount portion.

Disposed between the end member 17 and the rim 21 is a rotatable actuation ring 24 surrounding the cylindrical cam 18. A knob 25 is fixed to the outer periphery of the ring 24. A pin 26 extends inward from the actuation ring 24 and engages a helical groove 27 formed in the outer peripheral surface of the cylindrical cam 18. The stroke of the cylindrical cam 18 is selected as follows. As the actuation ring 24 is rotated clockwise as viewed from the camera mount in FIG. 1, the cam 18 is moved leftward in FIG. 1 under the guidance of the pin 26 engaging the groove 27. The left end surface of the cam 18 first hits against the projecting portion 16 of the engaging elements 11, and thereafter pushes the portion 16 to the left hand in FIG. 1 to rotate the engaging elements 11 counterclockwise. The elements 11 are rocked out of the cavity 4, i.e., out of the passage of the ocular portion 2 before the pin 26 reaches the right end of the groove 27 in FIG. 1. The cylindrical cam 18, slot 19, spring 23, actuation ring 24, pins 20 and 26, groove 27, and knob 25 constitute a releasing means.

In an embodiment as shown in FIG. 2, the cam surface 14 of each engaging element 11 is arcuate, and its center of curvature $O_1$ is separated toward the cylindrical cam 18 (i.e., toward the camera mount) from the center of rotation (or pivotal point $O_2$ of the element 11 or the pivot 12 so that the distance between the center of rotation $O_2$ and the cam surface 14 increases toward the cylindrical cam 18.

When the ocular portion 2 is not inserted in the cavity 4, the engaging elements 11 are further rotated clockwise from the position of FIG. 1 and protrude more towards the central axis l. As the ocular portion 2 is inserted into the cavity 4 it rocks the engaging elements 11 counterclockwise in FIG. 1 against the urging force of the springs 13. Then, the edge portion 7 of the ocular portion 2 engages the cylindrical inner wall surface 6 of the adapting portion 9 of the tube 1, and at the same time the front end surface of the edge portion 7 is brought into contact with the end surface of the flange 8 opposed to the front end surface of the edge portion 7. Thus, the ocular portion 2 is set in position in the cavity 4. At this time the cam surfaces 14 of the engaging elements 11 contact the conical rear surface 15 of the ocular portion 2, and thrust the ocular portion 2 into the tube 1 by means of the urging force of the springs 13, thereby keeping the ocular portion 2 in position.

When a pulling-out force is applied to the ocular portion 2, the conical rear surface 15 acts as a wedge on the cam surfaces 14 of the engaging elements 11. The pulling-out force is divided into component forces F which act perpendicularly to the conical rear surface 15 of the ocular portion 2 at a point P of the engaging elements 11 contacting the surface 15 and are directed to the center of curvature $O_1$, as shown in FIG. 2. The force F can be divided into two component forces $F_1$ and $F_2$, the component force $F_1$ being directed from the point P to the center of rotation $O_2$ of the engaging element 11, and the component force $F_2$ acting from the point P to the cylindrical cam 18 perpendicularly to the component force $F_1$. The component force $F_2$ tends to rotate the engaging element 11 counterclockwise about the center of rotation $O_2$. The materials of the engaging elements 11 and the rear surface portion of the ocular portion 2 are so selected as to provide the undermentioned coefficient of friction $\mu$, thereby to prevent the rotation of the engaging element 11 resulting from the component force $f_2$.

$$\mu \geq \sin\theta \cdot \cos\theta = (1/2)\sin 2\theta.$$

where $\theta$ is defined as an angle between the component forces $F_1$ and $F_2$. Thus, the ocular portion 2 would not be pulled off the camera mounting device, even if a large pulling force is exerted on the ocular portion 2.

Subsequently, when the knob 25 or actuation ring 24 is manually turned counterclockwise as viewed from the camera mount in FIG. 1, the cylindrical cam 18 is moved to the left hand under the guidance of the pins 20, 26 engaging the slot 19 and helical groove 27, respectively, and pushes with its left end the projecting portions 16 of the engaging elements 11 to thereby rock the elements 11 counterclockwise out of the cavity 4. Thus, the ocular portion 2 is disengaged from the cavity 4 without any interference with the elements 11.

As will be clear from the above description, attaching and detaching of the ocular portion 2 to and from the camera mounting device is quite easily and unfailingly accomplished by a single-handed operation of an operator.

What is claimed is:

1. A camera mounting device for an endoscope comprising:
    a connecting tube having one end fitted with a camera mount and the other end fitted with a conical ocular portion of an endoscope;
    an adapting portion provided on said other end of the connecting tube and having formed therein a cavity for receiving the ocular portion and a peripheral wall; and
    a connecting mechanism comprising
    engaging elements pivoted at a pivotal point to said peripheral wall of the adapting portion for swinging in a plane including a central axis of the connecting tube, each of said engaging elements having an arcuate convex cam surface formed on that end of the respective engaging elements which is nearer the central axis, said cam surface having a center of curvature separated from the pivotal point toward said one end of the connecting tube so that the cam surface is progressively separated from the pivotal point toward said one end of the connecting tube, and
    urging means provided on the adapting portion for resiliently urging the engaging elements in a direction in which the arcuate convex cam surfaces of the engaging elements abut against the outer surface of the ocular portion.

2. A camera mounting device according to claim 1, wherein said connecting mechanism includes releasing means comprising a cylindrical member surrounding said other end of the connecting tube and movable therealong for rocking said engaging elements out of said cavity when said cylindrical member is moved toward said engaging elements, and a guide element disposed between said cylindrical member and said connecting tube for guiding the cylindrical member along said connecting tube.

3. A camera mounting device according to claim 2, wherein said releasing means further comprises a helical groove formed in the outer periphery of said cylindrical member, an actuation ring surrounding said cylindrical member and rotatable about the central axis of the connecting tube, and a pin extending from said actuation ring toward said cylindrical member and engaging said helical groove.

4. A camera mounting device according to claim 3, wherein said cylindrical member is urged in an opposite direction to an direction in which said cylindrical member faces said engaging elements.

* * * * *